United States Patent [19]

Hopkins

[11] 4,341,802
[45] Jul. 27, 1982

[54] PRODUCTION OF PROTEIN WITH REDUCED NUCLEIC ACID

[75] Inventor: Thomas R. Hopkins, Bartlesville, Okla.

[73] Assignee: Provesto Corporation, Bartlesville, Okla.

[21] Appl. No.: 200,367

[22] Filed: Oct. 24, 1980

[51] Int. Cl.³ .............................................. A23L 1/28
[52] U.S. Cl. .................................. 426/60; 260/112 R; 426/61; 426/62; 426/656; 435/270; 435/804
[58] Field of Search ...................... 426/60, 61, 62, 656; 435/270, 804; 260/112 R

[56] References Cited

U.S. PATENT DOCUMENTS

| | | | |
|---|---|---|---|
| 3,585,179 | 6/1971 | Samejima et al. | 260/112 R |
| 3,634,194 | 1/1972 | Frankenfeld et al. | 195/28 N |
| 3,686,144 | 8/1972 | Tamura et al. | 260/112 R |
| 3,809,776 | 5/1974 | Chao | 435/270 X |
| 3,867,555 | 2/1975 | Newell et al. | 426/60 |
| 3,887,431 | 6/1975 | Robbins et al. | 426/60 X |
| 3,982,998 | 9/1976 | Hitzman et al. | 435/804 X |
| 3,996,104 | 12/1976 | Lindblom et al. | 435/270 X |
| 4,007,088 | 2/1977 | Fencl et al. | 435/270 X |
| 4,021,303 | 5/1977 | Nakabayashi | 426/656 X |
| 4,133,904 | 1/1979 | Steer et al. | 426/62 X |

FOREIGN PATENT DOCUMENTS 1372870 11/1974 United Kingdom .
1578235 11/1980 United Kingdom .

OTHER PUBLICATIONS

Miguel A. Otero et al., Biotechnology Letters, vol. 2, No. 9, pp. 379–384, 1980.
L. Viikari and M. Linko, Process Biochemistry, vol. 12, No. 4, Reduction of Nucleic Acid Content of SCP, pp. 17–20, 1977.
J. A. Zee and R. E. Simard, Applied Microbiology, vol. 29, No. 1, pp. 59–62, 1975.

Primary Examiner—Robert J. Warden

[57] ABSTRACT

Microorganisms with low nucleic acid content are produced by acid treating of the microorganism. One embodiment relates to the extraction of so treated microorganisms after their separation from the acid treating fluid, using a strong base for the extraction. Another embodiment relates to the neutralization of the acid treating fluid containing nucleic acids prior to the introduction of this fluid into the fermentation zone, the anion of the acid and the metal cation used in the neutralization step forming minerals desirable for the growth medium in the fermentation step.

16 Claims, 2 Drawing Figures

PRODUCTION OF PROTEIN WITH REDUCED NUCLEIC ACID

This invention relates to fermentation processes. More specifically this invention relates to methods for producing protein having reduced nucleic acid content and specifically proteins useful for human consumption.

BACKGROUND OF THE INVENTION

Biological and particularly fermentation processes have been used for centuries for instance in the art of beer brewing. Recently, such biological processes have attracted considerable interest for the production of protein both as feed supplements and ultimately for human consumption. It is known that one of the obstacles in using fermentation processes for the production of single cell protein for human consumption is the high content of nucleic acid of the single cell protein.

Various methods have been proposed in the art for the reduction of the nucleic acid content of the protein. Among those methods are treatment with alkali, treatment with acids, treatment with heat shock of the protein containing cells. Whereas certain details are known from these various methods for the reduction of the content of nucleic acids in single cell protein no integrated process has been disclosed or suggested by the prior art which would allow the production of Nucleic Acid Reduced Protein (NARP) in good yields while utilizing only a limited number of process steps.

THE INVENTION

It is therefore one object of this invention to provide a process for the production of protein having reduced nucleic acid content (NARP) as compared to the starting protein.

A further object of this invention is to provide a process for producing a microorganism cell product with improved utilization of both the carbon source and the mineral medium, as compared to known processes.

Yet a further object of this invention is to provide a process for the production of functional protein, and particularly of soluble protein with relatively low nucleic acid content having good functional properties such as whipability, and acceptable taste and color.

These and other objects, advantages, details, features and embodiments of this invention will become apparent to those skilled in the art from the following detailed description of the invention, the appended claims and the drawing in which

In accordance with this invention it has now been found that single cell protein after treatment with acids and heat not only have reduced nucleic acid content but that these cells also can very efficiently be extracted with a base resulting in a solution of water soluble NARP and therein suspended solid NARP which can be separated into these two products.

Thus, in accordance with a first embodiment of this invention a process for the production of protein having reduced nucleic acid content (NARP) is provided for. In this process a single cell protein mixture containing cells with high nucleic acid content and liquid are subjected to a nucleic acid removal step wherein at least a significant portion of the nucleic acids in the cells is transferred into the liquid. During this step the cells remain essentially intact and are easily centrifuged or filtered. This step produces a mixture of cells with reduced nucleic acid content and a nucleic acid containing fluid. The cells with reduced nucleic acid content are separated from the nucleic acid containing fluid. In accordance with this invention these cells are then extracted with a base at a pH of about 10.6 or more to obtain a NARP mixture of a liquid and a solid phase. The liquid phase is recovered as a NARP solution as a first product of the process and the solid phase is recovered as a NARP product as the second product of the process.

The soluble NARP can be utilized in various food products as a replacement for or supplement to egg white, casein or other soluble animal or plant protein fraction. The solid cell residue NARP can be used as a protein enriching ingredient in the production of food products. Both NARP products, i.e. the water soluble NARP and the solid cell residue NARP are useful for human consumption. Among the procedures to force the nucleic acids at least to a significant portion out of the cells into the surrounding fluid without rupturing the cells it is presently preferred to subject the cells to a treatment with acid and heat. Particularly, advantageous is a treatment of the single cell protein mixture with mineral acids at elevated temperatures. In accordance with a second embodiment of this invention a process for the production of cells of reduced nucleic acids is provided for. In this process a microorganism and a growth medium containing minerals are subjected to fermentation conditions together in a fermentation zone. An effluent is withdrawn from this fermentation zone and introduced into an acidifying zone together with an acid. After incubation at elevated temperature for a fixed period of time, the acidified mixture of a nucleic acids containing liquid phase and a solid cell phase is withdrawn. After this acid treatment the two phase mixture is separated into a liquid phase which is essentially free of microorganism cells and a cell rich phase. The cell phase has a reduced content of nucleic acids as compared to the cells in the effluent leaving the fermentation zone, but an essentially unchanged content of protein as compared to these cells prior to their acidification. At least a portion of this liquid phase containing soluble nucleic acids and being essentially free of cell material is introduced back into the fermentation zone. This process is improved in accordance with this invention by neutralizing the liquid nucleic acid containing phase prior to the introduction of the portion of this phase into the fermentation zone. This neutralization is carried out with an oxide, hydroxide, carbonate or bicarbonate of one or more metals or equivalents of metals. The acid and the base utilized, respectively, for the acid treatment and the neutralization step will be such that the neutralization step will form one or more of the minerals which are either already present or desirable in this growth medium in the fermentation zone. This second embodiment of this invention allows efficient use of the mineral medium which is reintroduced into the fermenter. In addition, however, the process of this invention also provides for a pH adjustment of the liquid phase introduced into the fermenter which pH adjustment simultaneously results in the supply of some of the desired minerals in the fermentation step. Furthermore, the nucleic acids are introduced into the fermenter where they serve as a carbon, nitrogen and phosphorous source. The overall efficiency of the process in this embodiment is therefore significantly enhanced.

The following details concerning the process are generally preferred in both embodiments of this invention described above.

The process of the present invention can be utilized with microorganisms capable of producing non-toxic single cell protein. Suitable microorganisms include bacteria, yeasts, and fungi. Yeasts are presently preferred.

Suitable yeasts include species from the genera Candida, Hansenula, Torulopsis, Saccharomyces, Pichia, Debaryomyces, Lipomyces, Crytococcus, Nematospora, and Brettanomyces. The preferred genera include Candida, Hansenula, Torulopsis, Pichia and Saccharomyces. Examples of suitable species include:

| | |
|---|---|
| Candida boidinii | Hansenula saturnus |
| Candida mycoderma | Hansenula californica |
| Candida utilis | Hansenula mrakii |
| Candida stellatoidea | Hansenula silvicola |
| Candida robusta | Hansenula polymorpha |
| Candida claussenii | Hansenula wickerhamii |
| Candida rugosa | Hansenula capsulata |
| Brettanomyces petrophilium | Hansenula glucozyma |
| Hansenula minuta | Hansenula henricii |
| Hansenula nonfermentans | Pichia membranefaciens |
| Hansenula philodendra | Pichia pinus |
| Torulopsis candida | Pichia pastoris |
| Torulopsis bolmii | Pichia trehalophila |
| Torulopsis versatilis | Saccharomyces cerevisiae |
| Torulopsis glabrata | Saccharomyces fragilis |
| Torulopsis molishiana | Saccharomyces rosei |
| Torulopsis nemodendra | Saccharomyces acidifaciens |
| Torulopsis nitratophila | Saccharomyces elegans |
| Pichia farinosa | Saccharomyces rouxii |
| Pichia polymorpha | Saccharomyces lactis |
| | Saccharomyces fractum |

Suitable bacteria include species from the genera Bacillus, Mycobacterium, Actinomyces, Nocardia, Pseudomonas, Methanomonas, Brevibacterium, Acetobacter, Micrococcus, Rhodopseudomonas, Corynebacterium, Microbacterium, Achromobacter, Methylobacter, Methylosinus, and Methylocystis. Preferred genera include Bacillus, Pseudomonas, Protaminobacter, Micrococcus, Arthrobacter and Corynebacterium.

Examples of suitable species include:

| | |
|---|---|
| Bacillus subtilus | Pseudomonas ligustri |
| Bacillus cereus | Pseudomonas orvilla |
| Bacillus aureus | Pseudomonas methanica |
| Bacillus acidi | Pseudomonas fluorescens |
| Bacillus urici | Pseudomonas aeruginosa |
| Bacillus coagulans | Pseudomonas oleovorans |
| Bacillus mycoides | Pseudomonas putida |
| Bacillus circulans | Pseudomonas boreopolis |
| Bacillus megaterium | Pseudomonas pyocyanea |
| Bacillus licheniformis | Pseudomonas methylphilus |
| Pseudomonas methanolica | Pseudomonas brevis |
| Pseudomonas acidovorans | Methylomonas agile |
| Pseudomonas methanoloxidans | Methylomonas albus |
| Pseudomonas aerogenes | Methylomonas rubrum |
| Protaminobacter ruber | Methylomonas methanolica |
| Corynebacterium simplex | Mycobacterium rhodochrous |
| Corynebacterium hydrocarbooxydans | Mycobacterium phlei |
| Corynebacterium alkanum | Mycobacterium brevicale |
| Corynebacterium oleophilus | Nocardia salmonicolor |
| Corynebacterium hydrocarboclastus | Nocardia minimus |
| Corynebacterium glutamicum | Nocardia corallina |
| Corynebacterium viscosus | Nocardia butanica |
| Corynebacterium dioxydans | Rhodopseudomonas capsulatus |
| Corynebacterium alkanum | Microbacterium ammoniaphilum |
| Micrococcus cerificans | Archromobacter coagulans |
| Micrococcus rhodius | Brevibacterium butanicum |
| Arthrobacter rufescens | Brevibacterium roseum |
| Arthrobacter parafficum | Brevibacterium flavum |
| Arthrobacter simplex | Brevibacterium lactofermentum |
| Arthrobacter citreus | Brevibacterium paraffinolyticum |
| Methanomonas methanica | Brevibacterium ketoglutamicum |
| Methanomonas methanooxidans | Brevibacterium insectiphilium |

Suitable fungi include species from the genera Aspergillus, Monilia, Rhizopus, Penicillium, Mucor, Alternaria and Helminthosporium.

Examples of suitable species of fungi include:

| | |
|---|---|
| Aspergillus niger | Penicillium griseofulvum |
| Aspergillus glaucus | Penicillium expansum |
| Aspergillus flavus | Penicillium digitatum |
| Aspergillus terreus | Penicillium italicum |
| Aspergillus itconicus | Rhizopus nigricans |
| Penicillium notatum | Rhizopus oryzae |
| Penicillium chrysogenum | Rhizopus delemar |
| Penicillium glaucum | Rhizopus arrhizus |
| Rhizopus stolonifer | Mucor mucedo |
| Mucor genevensis | |

In the practice of the process of the present invention, the microorganism, the source of carbon and energy in the growth of the microorganism, and fermentation conditions and procedures are not believed to be critical. The fermentation conditions and source of carbon and energy as known in the art or as determined for the particular microorganism chosen should be employed.

Methanol fermentation using bacteria is for instance described in U.S. Pat. No. 3,982,998. A fermentation involving a yeast is described in detail in U.S. Pat. No. 4,168,201. Both patents are herein incorporated by reference.

NUCLEIC ACID REMOVAL

According to the process of this invention the fermenter effluent is treated in a nucleic acid reduction step. Any nucleic acid reduction method can be used that does not cause extensive (or significant) cell disruption and that reduces the nucleic acid level to below about 2 weight percent. Examples of methods of removing nucleic acids include (a) acid treatment
(b) base treatment
(c) heat shock and enzymatic action.

These nucleic acid reduction methods have been reported previously, see e.g. L. Viikari and M. Linko, Process Biochemistry, May 1977, pp. 17, 18, 19, 35; and J. A. Zee and R. E. Simard, Applied Microbiology, 29, 59–62 (1975).

One convenient method of nucleic acid reduction is a treatment with acid. The use of an acid treatment has been found to be simple, reliable, and economical. Any suitable mineral acid, such as sulfuric acid, hydrochloric acid, phosphoric acid, and the like, can be used. The acid is added to the fermenter effluent to a concentration of about 0.2 to about 4 normal (N). Temperatures between about 50° and about 100° C. are satisfactory. The reaction time for the acid treatment will depend on the acid concentration, the mineral acid used, and temperature, but will generally be from about 10 minutes and several hours.

When the liquid stream from the separation step following the acid treatment is to be recycled to the fermenter, the choice of acid will frequently be so as to provide the anion used in the mineral feed for the fermentation. Thus, when the mineral feed contains phosphate salts, phosphoric acid would be used in the acid treatment. Likewise, when sulfate salts are used in the mineral feed, sulfuric acid would be used in the acid treatment.

It has been determined that when milder conditions (lower acid concentrations, e.g. 0.4 N, or lower reaction temperatures, e.g. 80° C.) are used in the acid treatment step, it is strongly preferred to add base to the acidic mixture before separation to adjust the pH to about 7 to 9 to allow the relatively rapid release of the hydrolyzed nucleic acids from the cells. Under stronger conditions of higher acid concentrations, e.g. 0.8 N, or higher temperatures, e.g. 95° C., the base addition before the separation step is preferred also but is not as essential. In the latter situation, base would be added to the liquid stream from the separation stage to adjust the pH to an acceptable level before recycling the liquid to the fermenter. A reasonable contact time between the acid treated cell material and the base is significant. Usually the contact times greater than one minute are desirable.

While the base employed in the above described base additions can be any suitable base, such as NaOH, KOH, Ca(OH)$_2$, Mg(OH)$_2$, NH$_4$OH, and the like, it is frequently advantageous when the liquid stream from the separation step is to be recycled to the fermenter to use the hydroxides or oxides of metals used in the mineral media feed for the fermenter. Carbonates and bicarbonates may also be used; typical metals or equivalents of metals to be contemplated are Ca, K, Na, Mg, Fe, Cu, Zn, Mn and NH$_4$. For example, when the mineral medium feed contains K$_2$SO$_4$ and MgSO$_4$, the acid in the acid treatment would be H$_2$SO$_4$ and the base would be a mixture of KOH and Mg(OH)$_2$. This provides needed minerals for growth of the microorganism and avoids the introduction of salts not needed by or perhaps even toxic to the microorganism.

The mixture from the nucleic acid reduction step is separated using techniques, such as centrifugation or filtration, to produce a cellular fraction with a lower nucleic acid level than the original cells and a liquid stream containing nucleic acids. The cellular fraction is then treated with an aqueous base for protein extraction. At least a portion of the liquid stream from the separation step is recycled to the fermenter, normally with the pH adjusted to the desired level for the particular microorganism employed.

SOLUBLE PROTEIN EXTRACTION

The nucleic acid reduced cells are treated with an aqueous base under conditions suitable for the extraction of a portion of the protein. Suitable bases include KOH, NaOH, Ca(OH)$_2$, NH$_4$OH, K$_2$CO$_3$ and the like. The protein extraction conditions are generally a pH above about 10.6, a temperature between about 0° and about 80° C., and an extraction time between a few minutes and several hours. The bases utilized have a normality usually in the range of 0.5 N to 15 N, and preferably 1 N to 5 N.

The currently preferred base for the protein extraction is ammonium hydroxide. The stronger bases, such as NaOH, have been reported to cause the formation of lysinoalanine, which may result in kidney lesions in humans. In addition, the use of bases such as NaOH results in an increase in the salt content of the isolated soluble protein. Ammonium hydroxide appears to greatly diminish the formation of lysinoalanine and excess ammonia can be removed from the soluble protein during the drying step.

At the conclusion of the protein extraction step the resulting mixture is separated into a liquid stream containing the extracted protein and a proteinaceous solid which is the extracted cellular material. The separation can be accomplished by such methods as centrifugation or filtration.

The solid from the separation can be dried, e.g., by a spray dryer, to provide a dry material containing protein, fiber, lipids, and carbohydrates. This material is low in nucleic acids and is suitable for use in animal feed or bulk protein supplement in human foods.

The liquid stream from the separation step can be dried, e.g., by a spray dryer, to remove the water and to yield a dried, soluble protein with a much lower nucleic acid level than would have been present in the absence of the nucleic acid removal step. This protein is tasteless, odorless, and off-white in color. It has desirable functional properties similar to the properties of egg white and other high quality proteins and can be employed in various foods.

Figure 1:
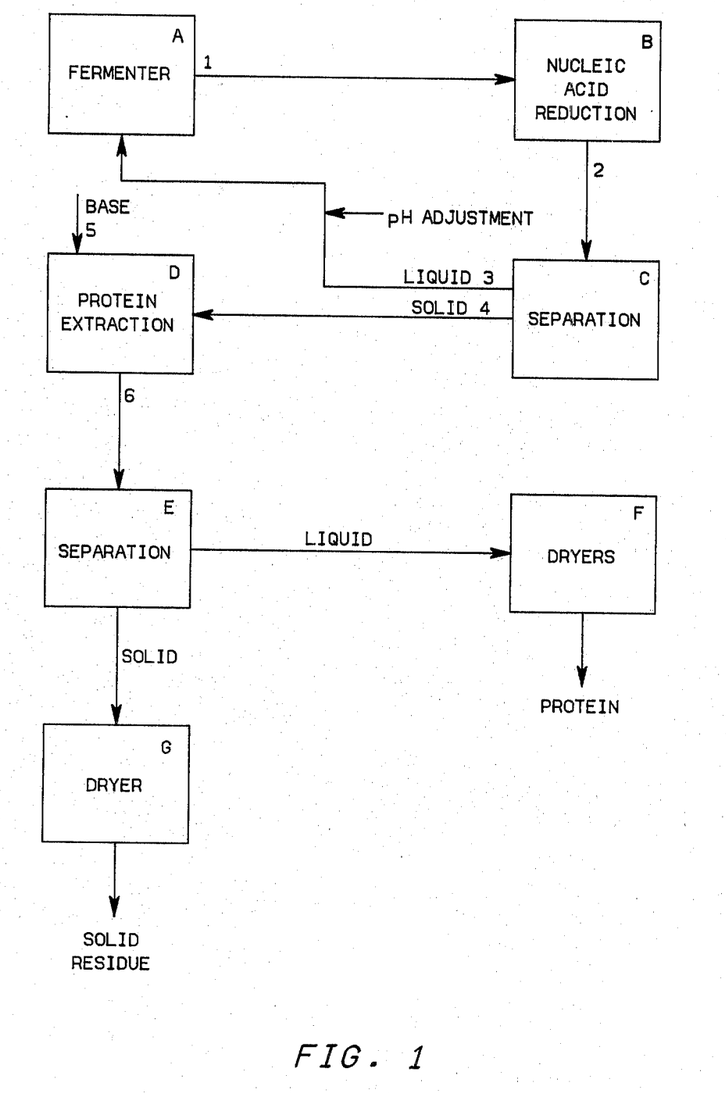
FIGS. 1 and 2 are schematic flow schemes illustrating the processes of this invention.
Figure 2:
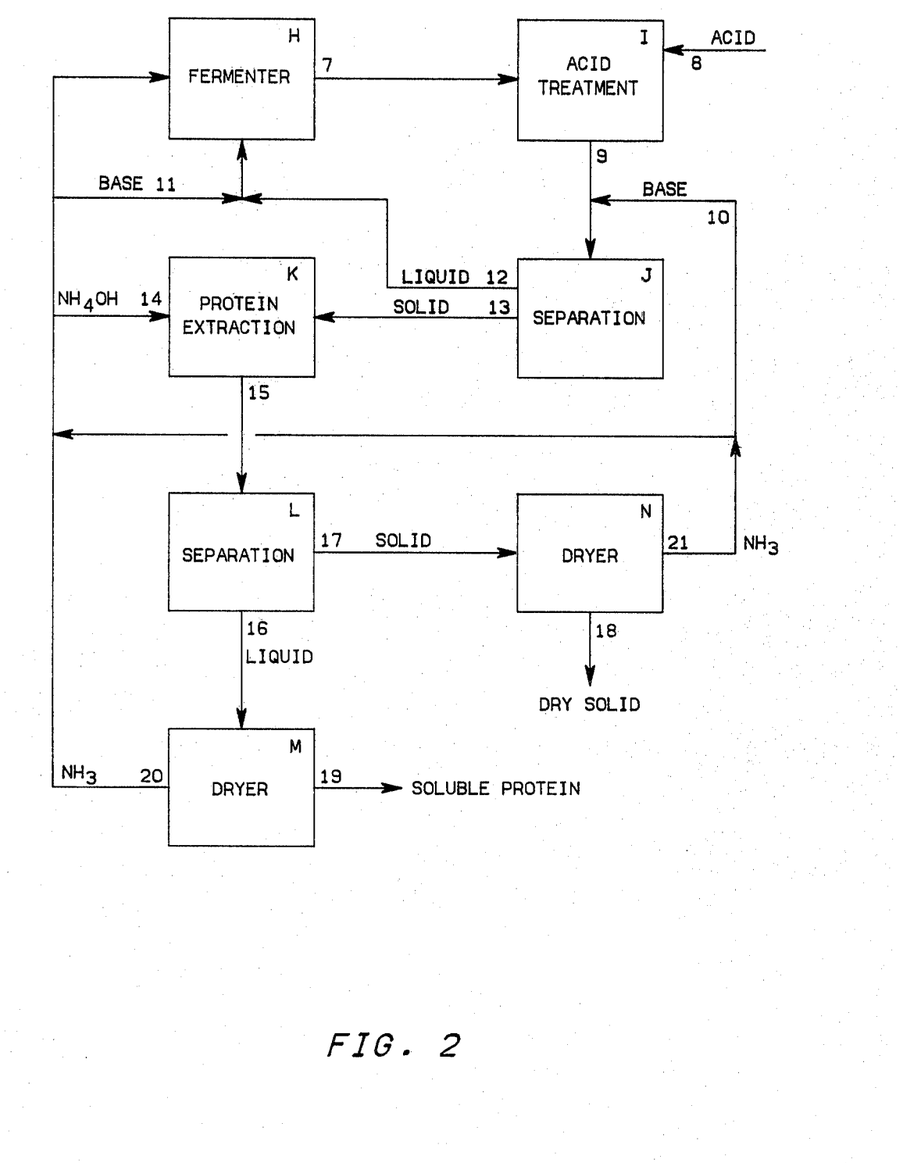

When ammonium hydroxide is used in the protein extraction step, the ammonia removed during the product drying steps can be collected, e.g., by condensation or by absorption in water, and recycled to other points in the process such as the fermenter A in FIG. 1 or fermenter H or points 10, 11 or 14 in FIG. 2.

The process of the present invention is described in FIG. 1. The fermenter effluent from the fermentation with a microorganism in fermenter A is passed 1 to a nucleic acid reduction step B. At the conclusion of the nucleic acid reduction step, the product is passed 2 with or without a neutralization step to a separation stage C, such as a centrifuge, where the nucleic acid reduced cells are separated from the nucleic acid containing fluid. The fluid can be at least partially recycled 3 to the fermenter A, usually with a pH adjustment, to provide nucleic acids, vitamins, and minerals for the growing microorganism in the fermentation zone. The nucleic acid reduced cells are transferred 4 to the base treatment stage D where a suitable base is added 5 and the cells are treated under conditions suitable for extracting the soluble protein. At the conclusion of the extraction step, the product mixture is passed 6 to a separation stage E, such as a centrifuge, where the mixture is separated into a liquid phase containing soluble protein and a solid containing the proteinaceous cell residues. The soluble protein can be used if desired as the aqueous solution or can be dried F to isolate the protein. Likewise, the proteinaceous solid residue from the separation can be used as the moist solid or dried G to provide a dry, protein containing residue.

In a more specific example of the process of the present invention, FIG. 2 describes a process involving an acidic nucleic acid reduction step and an ammonium hydroxide protein extraction step. The effluent from a fermenter H is transferred 7 to an acid treatment stage I where an acid is introduced 8. Following the acid treatment under conditions suitable for the reduction of the nucleic acid level of the cells, the treated mixture is sent 9 to a separation stage J. A base can be added 10 to the treated mixture to adjust the pH to near neutrality or base can be added 11 to the liquid stream 12 from the separation stage. The liquid stream 12 is completely or partially recycled to the fermenter to provide extracted nucleic acids as well as vitamins and minerals from the fermenter effluent for the growing microorganism.

The nucleic acid reduced cells 13 from the separation stage J are treated K with ammonium hydroxide or anhydrous ammonia 14 under suitable conditions to extract the soluble protein from the cells. At the conclusion of the extraction step, the product mixture 15 is separated L, e.g. by centrifuge, to produce a liquid 16 containing the soluble protein and a residual protein containing material 17. The products can be used as received from the separation L or can be dried M and N to yield the dried, residual proteinaceous solid 18 and dried soluble protein 19. If desired, ammonia from the dryers M and N can be collected 20 and 21 and recycled to the fermenter H or to points of base addition 10, 11, or 14.

The following examples are intended to illustrate further preferred details of the invention without undue limitation of its scope.

EXAMPLES

The nucleic acid levels were determined by perchloric acid extraction and spectrophotometric analysis at 260 nm.[2] The protein contents were determined by an extraction with NaOH at 100° C., in the presence of $CuSO_4.5H_2O$, and the measurement of the absorbance of the protein-copper complex at 540 nm using bovine albumin serum as a standard.[2]

The fermenter effluent used in some of the examples was from the continuous fermentation of a *Pichia pastoris* yeast culture which has been deposited with the official depository, United States Department of Agriculture, Agriculture Research Service, Northern Regional Research Laboratory, Peoria, Ill. 61604 and is designated as NRRL Y-11430. The fermentation was carried out at about 30° C. using a methanol feedstock and had a cell density of about 125 g of cells (dry weight) per liter of effluent.

The fermenter effluent used in other examples was a thermophilic mixed bacteria culture HTB-53 which is deposited as NRRL B-8158. This thermophilic mixed culture of bacteria is the subject of Application Ser. No. 856,545 filed Dec. 1, 1977, which is a continuation of Ser. No. 698,251, filed June 21, 1976, now abandoned. The bacteria are individually classified as (1) a large gram-positive curved rod, division Bacteria, class Schizomycetes, order Eubacteriales, family Bacillaceae, genus Bacillus; (2) a large gram-negative rod, division Bacteria, class Schizomycetes, order Eubacteriales, family Bacillaceae, genus Bacillus; (3) a short gram-negative rod, division Bacteria, class Schizomycetes. This mixed thermophilic bacteria was grown in a continuous fermentation at about 55° C. with methanol as the source of carbon and energy. The cell density during the fermentation was about 45 g (dry weight) per liter of fermenter broth.

EXAMPLE I

A run was carried out to demonstrate the process of the present invention. In run 1, a reaction vessel was charged with 50 mL of the fermenter effluent from the growth of *Pichia pastoris* and 0.6 mL of concentrated sulfuric acid to form a mixture which was 0.43 N in sulfuric acid. The mixture was heated to 80° C. for 30 minutes and then a saturated sodium hydroxide solution was added to adjust the pH to 8.7. After about 10 minutes, the mixture was centrifuged (the supernatant was saved for a later analysis) and the centrifuge pellet was washed with distilled water. The washed pellet was resuspended in distilled water (total volume of 50 mL) and 6 mL of concentrated ammonium hydroxide solution was added to the suspension to form a mixture which was 1.61 N in ammonium hydroxide. This suspension was heated at 50°–80° C. for 30 minutes and was then centrifuged to yield an aqueous supernatant containing functional soluble protein and a residual proteinaceous pellet.

Several of the products from this run were analyzed for protein, nucleic acids, ash, and other components. The results are presented in Table I in terms of the composition of 100 g of the original single cell protein and the final distribution of the components in the various process products.

TABLE I

|  | Original Cells | Soluble Functional Protein | Residual Protein | Soluble Waste[a] |
|---|---|---|---|---|
| Protein | 52 g | 10 g | 33 g | 6 g |
| Nucleic Acids | 5 | 0.6 | 0.2 | 4 |
| Ash | 12 | 1.1 | 1.3 | 10[b] |
| Miscellaneous | 31 | 0.1 | 16 | 13 |
| Total | 100 g | 11.8 g | 50.5 g | 33 g.[b] |

[a]Centrifuge supernatant after acid treatment.
[b]The $Na_2SO_4$ introduced during the effluent process is not included in these weights.
[c]Fiber, lipids, and carbohydrates.

These results demonstrate the process of the present invention for the formation of a soluble functional protein and a residual protein with low nucleic acid levels. Most of the original nucleic acid from the SCP is found in the centrifuge supernatant after the acid treatment step. In the absence of an acid treatment step, most of the nucleic acids would be present in the soluble functional protein fraction (see Example III).

EXAMPLE II

Another run was carried out in accordance with the process of the present invention. In run 2, a stainless steel reaction vessel was charged with 3 liters of the fermenter effluent from the fermentation of *Pichia pastoris* (5.9 g/L nucleic acids and 66.8 g/L protein) and 36 mL of concentrated sulfuric acid to form a mixture which was 0.43 N in sulfuric acid. The mixture was heated to 80° C., held at 80° C. for 30 minutes, treated with saturated sodium hydroxide solution to pH 8 to 9, and allowed to stand for 10 minutes. Centrifugation of the mixture was carried out and the centrifuge pellet was washed with water. The nucleic acid reduced protein (as an aqueous suspension) contained 54.1 g/L protein and only 0.5 g/L nucleic acids. Concentrated ammonium hydroxide was added to a suspension of the protein to yield a concentration of 1.84 N ammonium hydroxide. This suspension was heated to 55° C., held at 55° C. for about 15 minutes, and centrifuged. The supernatant (13 g/L protein and 1 g/L nucleic acids) was dialyzed against water to remove salts and was then freeze dried to yield the functional protein.

EXAMPLE III

Several runs were carried out to demonstrate the importance of the nucleic acid removal step before the soluble protein extraction step and to compare different nucleic acid reduction procedures. The treatment steps utilized in each run are summarized below.

| Run | Nucleic Acid Reduction | Soluble Protein Extraction |
|---|---|---|
| 3 | none | NH₄OH (1.84 N) |
| 4 | H₃PO₄ (0.93 N) | NH₄OH (1.84 N) |
| 5 | NH₄OH (0.2 N) | NH₄OH (1.84 N) |

Each run used the fermenter effluent from the fermentation of *Pichia pastoris*. In run 4, 30 mL of the fermenter effluent was mixed with 0.6 mL of 85% H₃PO₄ to give a mixture 0.93 N in H₃PO₄. This mixture was heated at 85° C. for 1 hour, adjusted to pH 8 with concentrated NH₄OH, and allowed to stand at room temperature (about 25° C.) for 1 hour. The mixture was centrifuged and the pellet was washed with water.

In run 5, 30 mL of the fermenter effluent was mixed with 0.42 mL of concentrated NH₄OH to give a mixture 0.21 N in NH₄OH. This mixture was heated at 95° C. for 1 hour, centrifuged, and the centrifuge pellet was washed with water.

In all three runs, 25 mL of a cell suspension (fresh cells in run 3, H₃PO₄ treated cells in run 4, NH₄OH treated cells in run 5) was mixed with 3.5 mL of concentrated NH₄OH to yield a mixture 1.84 N in NH₄OH. The mixture was heated to 80° C. for about 10 minutes and then centrifuged to yield a supernatant containing functional protein and a pellet which is the residual protein. The assay results from the various products are summarized in Table II.

TABLE II

| | | After Nucleic Acid Reduction | | Residual Protein | | Functional Protein | |
|---|---|---|---|---|---|---|---|
| Run No. | Nucleic Acid Reduction | Nucleic Acids, g/L | Protein, g/L | Nucleic Acids, g/L | Protein, g/L | Nucleic Acids, g/L | Protein, g/L |
| 3 | none | — | — | 1.4 | 44 | 6.8 | 14.8 |
| 4 | H₃PO₄ | 0.9 | 53.3 | 0.3 | 38 | 2.1 | 13.0 |
| 5 | NH₄OH | 1.0 | 60.7 | 0.5 | 43 | 1.4 | 6.4 |

These results show that in the absence of a first nucleic acid reduction step (run 3), the extracted functional protein contains a high level of nucleic acids (about 30% nucleic acids). In runs 4 and 5, nucleic acid reduction steps using either H₃PO₄ or NH₄OH result in extracted functional protein with much lower nucleic acid levels. The low level of protein in the functional protein in run 5 suggests that the nucleic acid removal step using NH₄OH decreases the effectiveness of the protein extraction step.

EXAMPLE IV

Coconut macaroon cookies were prepared from functional protein extracted according to the process of the present invention. The functional protein used was the combined products from several runs similar to the run in Example I. This functional protein was dialyzed against water to remove salts and was lyophilized. The recipe used 8 g of protein in 60 mL water (the equivalent of 2 egg whites) ½ teaspoon vanilla, ⅜ cup sugar, and 1⅓ cup flaked coconut. After beating the protein with the vanilla, sugar was added and beating was continued until the mixture was stiff. After the coconut was added to the mixture, the mixture was allowed to stand for 10 minutes. Cookies were baked at 325° F. (163° C.) for 20 minutes. The resulting cookies had good appearance and taste. These results show that the protein extracted by the process of the present invention has functional properties similar to egg white.

EXAMPLE V

Run 6 was carried out according to the present invention for the extraction of protein from bacterial SCP. A mixture containing 0.4 N hydrochloric acid (HCl) was prepared from 2.9 liters of the fermenter effluent from the fermentation of the thermophilic bacteria mixture HTB-53 and 100 mL concentrated hydrochloric acid. The mixture was heated at 80° C. for 20 minutes and neutralized with 55 mL of saturated sodium hydroxide solution (50% w/v). Centrifugation of the mixture gave a supernatant and a pellet. The pellet was mixed with water and concentrated NH₄OH to a volume of 3 liters and NH₄OH concentration of 2.1 N. Heating this mixture for 20 minutes at 80° C. with occasional stirring followed by centrifugation gave a supernatant containing soluble protein and a pellet containing residual protein and other cellular materials. The assays of the various fractions during the process are presented in Table III. A sample of the fermenter effluent was centrifuged to provide a pellet and a supernatant for the first two samples.

TABLE III

| | Nucleic Acids | | Protein | |
|---|---|---|---|---|
| | g/L | %[a] | g/L | % of Total Starting Protein |
| Pellet from Effluent[b] | 5.12 | 12.5 | 30.0 | 96 |
| Supernatant from Effluent | 0.98 | 2.4 | 1.3 | 4 |
| Pellet from Acid Treatment[b] | 1.24 | 3.0 | 38.2 | 90 |
| Supernatant from Acid Treatment | 4.27 | 10.4 | 2.3 | 6 |
| Pellet from Extraction[b] | 0.49 | 1.2 | 25.2 | 52 |
| Supernatant from Extraction | 1.35 | 3.3 | 18.1 | 38 |

[a]Nucleic acids as a % of total solids (dry weight) of each fraction.
[b]The pellets were suspended in water for the assays.

These results show that the process of the present invention for removal of nucleic acid from SCP and the extraction of protein from the nucleic acid reduced protein is suitable for use with bacterial cells.

EXAMPLE VI

Example V was essentially repeated, utilizing however instead of the bacteria culture a yeast culture, namely a cell effluent of *Pichia pastoris*. The results of this example are shown in the following table.

TABLE IV

| | Nucleic Acids | | Protein | |
|---|---|---|---|---|
| | g/L | %[a] | g/L | % of Total Starting Protein |
| Pellet from Effluent[b] | 5.13 | 6.0 | 53.0 | 98 |
| Supernatant from Effluent | 0.09 | 1.1 | 0.91 | 2 |
| Pellet from Acid Treatment[b] | 1.44 | 1.7 | 49.0 | 84 |

TABLE IV-continued

| | Nucleic Acids | | Protein | |
|---|---|---|---|---|
| | | | | % of Total Starting |
| | g/L | %[a] | g/L | Protein |
| Supernatant from Acid Treatment | 5.08 | 6.0 | 7.87 | 14 |
| Pellet from Extraction[b] | 0.28 | 3.3 | 38.5 | 64 |
| Supernatant from Extraction | 1.16 | 1.3 | 12.1 | 20 |

[a] and [b] See footnotes for Table III

This example, too, shows that an effective reduction in the nucleic acid content is achieved and that both the pellet from the ammonium hydroxide extraction and the supernatant fluid constitute a protein product with reduced nucleic acid content as compared to the starting cell material from the effluent.

EXAMPLE VII

Example V was essentially repeated except as noted in the following.

For the acid digestion 30 mL concentrated $H_2SO_4$ (0.54 N) was used (instead of the HCl) per 45 mL of *Pichia pastoris* culture medium. The acid was added at 50° C. and the mixture was heated to 80° C. At 80° C. the water bath was turned off and the mixture was allowed to sit at 70°-80° C. for one hour. No neutralization step was carried out, but the mixture was centrifuged right away. The pellet was resuspended in about 2.5 L water. To this resuspended cell mixture 420 mL $NH_4OH$ were added at a temperature of 30° C. and the mixture was then heated to 80° C. At that temperature the mixture was held for one hour. The mixture had changed from yellow to a light green color. It appeared that a shorter $NH_4OH$ treatment time would have been preferable to avoid the color change. The results of this example are shown in the following Table V.

TABLE V

| | Nucleic Acids | | Protein | |
|---|---|---|---|---|
| | | | | % of Total Starting |
| | g/L | %[a] | g/L | Protein |
| Pellet from Effluent[b] | 7.18 | 5.9 | 69.1 | 97 |
| Supernatant from Effluent | .39 | 0.3 | 1.9 | 3 |
| Pellet from Acid Treatment[b] | 3.04 | 2.5 | 64.4 | 82 |
| Supernatant from Acid Treatment | 7.00 | 5.8 | 11.3 | 15 |
| Pellet From Extraction[b] | 0.92 | 1.0 | 50.6 | 62 |
| Supernatant from Extraction | 3.84 | 4.0 | 16.9 | 21 |
| Large scale centrifugation | 3.25 | 10.6 | 17.8 | — |
| Same (second sample) | 3.21 | 10.4 | 17.0 | — |
| Pellet from Extraction | 0.76 | 1.1 | 51.0 | — |

[a] See footnote for Table III
[b] See footnote for Table III

This example, too, shows that with the process of this invention two different products, both of reduced nucleic acid content, can be produced. The results also show that the data are well reproducible.

EXAMPLE VIII

Example V was again essentially repeated except as noted in the following. Thirty mL concentrated $H_2SO_4$ was added in this example at about 50° C., the mixture was heated to 80° C. and held at that temperature for 30 minutes. For neutralization, 68.5 g KOH (85%) was used and the final pH was determined to be 5.85. The acid treated and neutralized product was centrifuged at three thousand RPM for 5 minutes and washed once with hot water. To the solid cell material ammonium hydroxide was added at 40° C., the mixture was heated to 80° C. and held at that temperature for 30 minutes. The results are shown in the following table.

TABLE VI

| | Nucleic Acids | | Protein | |
|---|---|---|---|---|
| | | | | % of Total Starting |
| | g/L | %[a] | g/L | Protein |
| Pellet from Effluent[b] | 7.61 | 7.0 | 61.6 | 87 |
| Supernatant from Effluent | 0.33 | 0.3 | 9.5 | 13 |
| Pellet from Acid Treatment[b] | — | — | — | — |
| Supernatant from Acid Treatment | 7.23 | 5.3 | — | — |
| Pellet from Extraction | 0.45 | 0.6 | 43.8 | ~52 |
| Supernatant from Extraction | 2.26 | 3.2 | 14.6 | ~17 |

[a] and [b] See footnotes for Table III

EXAMPLE IX

The previous example was repeated except that 51 mL concentrated $H_2SO_4$ and 113 g KOH (85%) were used. The sulfuric acid was 0.6 normal. The results of this run are shown in the following table.

TABLE VII

| | Nucleic Acids | | Protein | |
|---|---|---|---|---|
| | | | | % of Total Starting |
| | g/L | %[a] | g/L | Protein |
| Pellet from Effluent[b] | 7.43 | 6.9 | 73.1 | 97 |
| Supernatant from Effluent | 0.40 | 0.37 | 2.0 | 3 |
| Pellet from Acid Treatment[b] | 3.18 | 2 | 71.2 | 83 |
| Supernatant from Acid Treatment | 7.92 | 5 | 12 | 14 |
| Pellet from Extraction[b] | 0.85 | 1.1 | 63.9 | 58 |
| Supernatant from Extraction | 2.51 | 3.1 | 28.0 | 25 |

Large scale centrifugation was carried out with the remaining $NH_4OH$-treated material.

| Supernatant from Extraction[b] | 2.11 | 2 | 27 | — |
| Pellet from Extraction | 0.55 | 0.5 | 58.4 | — |

[a] and [b] See footnotes for Table III

The two examples shown above indicate that functional protein having reduced nucleic acid content can be obtained by the process of this invention.

EXAMPLE X

This example describes a pilot plant run using effluent from a fermenter with *Pichia pastoris* as the yeast. The effluent was collected in a 90 gallon container and kept at a temperature of about 10° C. To this container 3.75 liters of concentrated $H_2SO_4$ was added. The contents of the container was heated to 80° C. and maintained at that temperature for 20 minutes. The final pH was 0.95. Then 8.64 kilogram KOH (85%) was added raising the pH to 3.85 and raising the temperature about 10° C. The processed fluid contains about 60 g/L *Pichia pastoris*. The product was processed in Merco[R], a continuous, washing, centrifuge and the stream split 3.5 (waste wash) to 0.9 (cell cream).

The separation was not optimum, i.e. the "solids" fraction of 90 gallons still contained a very considerable amount of liquid and thus retained some of the extracted nucleic acid. To this "solids" fraction 52 liters of $NH_4OH$ solution was added. The product obtained was again centrifuged, washed and split 6.0 to 1.5. The underflow ("solids" fraction) was diluted and passed through the centrifuge again without wash. The first supernatant was quite clear and good solids separation thus was possible.

The liquid was spray dried with an inlet temperature of 540° F. and an outlet temperature of 210° F.

The following results were obtained.

TABLE VIII

|  | Nucleic Acids | | Protein | % of Total Starting |
|---|---|---|---|---|
|  | g/L | %[a] | g/L | Protein |
| Pellet from Effluent[b] | 3.92 | 7.0 | 40.1 | 98 |
| Supernatant from Effluent | 0.015 | 0.2 | 0.7 | 2 |
| Pellet from Acid Treatment[b] | 1.75 | 4.4 | 36.1 | 82 |
| Supernatant from Acid Treatment | 3.13 | 12.0 | 6.9 | 16 |
| Pellet from Extraction[b] | 5.22 | 2.8 | 147.8 | 51 |
| Supernatant from Extraction | 5.6 | 10.8 | 26.1 | 31 |

[a] and [b] See footnotes for Table III

EXAMPLE XI

In the example, 5 mL of bacteria cell cream that has been washed once (HTB-53, the same cell cream as used supra in Example V) were acidified with 60 mL $H_2SO_4$ (0.4 N). This mixture was heated at 80° C. for 30 minutes. Thereafter, the mixture was "neutralized" with 0.1 mL saturated sodium hydroxide. The "neutralized" mixture was centrifuged and the pellets were resuspended in water. To this mixture 0.6 mL concentrated $NH_4OH$ was added and the mixture was maintained at 34.5° C. for 25 minutes. The so obtained mixture was phase separated in a centrifuge and the pellets and the supernatant was analyzed for the protein content. No nucleic acid content was determined in this example. The results obtained are shown in the following table:

TABLE IV

|  | Protein % of Total Starting Protein |
|---|---|
| Pellet from Effluent[a] | 93 |
| Supernatant from Effluent | 7 |
| Pellet from Acid Treatment[a] | 74 |
| Supernatant from Acid Treatment | 20 |
| Pellet from Extraction | 44 |
| Supernatant from Extraction | 24 |
| Pellet from Effluent (ammonium hydroxide extracted only)[b] | 60 |
| Supernatant from Effluent (ammonium hydroxide extracted only)[b] | 33 |

[a] The pellets were suspended in water for the assays.
[b] The washed cell cream was extracted with ammonium hydroxide directly as described above, but without prior acidification and neutralization.

EXAMPLE XII

The previous example was repeated except that the cell cream in this instance was an effluent from a fermenter utilizing the yeast *Pichia pastoris* as the microorganism. The results obtained are shown in the following table.

TABLE V

|  | Protein % of Total Starting Protein |
|---|---|
| Pellet from Effluent[a] | 97 |
| Supernatant from Effluent | 3 |
| Pellet from Acid Treatment[a] | 79 |
| Supernatant from Acid Treatment | 18 |

TABLE V-continued

|  | Protein % of Total Starting Protein |
|---|---|
| Pellet from Extraction[a] | 64 |
| Supernatant from Extraction | 13 |
| Pellet from Effluent (ammonium hydroxide extracted only)[b] | 76 |
| Supernatant from Effluent (ammonium hydroxide extracted only)[b] | 21 |

[a] The pellets were suspended in water for the assays
[b] The washed cell cream was extracted with ammonium hydroxide directly as described above, but without prior acidification and neutralization.

The results of the last two examples are believed to be not representative of the invention for the following reason. It is believed that the high quantity of protein extracted in the acid treatment step followed by the "neutralization" (20% and 18% respectively) was caused by too high a pH during the "neutralization" step. Therefore, the total quantities of extracted protein in the runs that were intended to be comparative runs are not representative. This assumption is based on later measurements of the dependency of the protein extraction upon the pH. These measurements have shown that the protein extraction increases rapidly for the above discussed microorganisms and operation conditions at a pH of about 10.5 whereas little protein is transferred from the cells into the liquid phase at pH values between about 5.4 and 8.

EXAMPLE XIII

In this example the effect of ammonium hydroxide as compared to sodium hydroxide on the cross linking of proteins is determined.

Two hundred and forty milligrams of chymotrypsinogen or 240 milligrams of ribonuclease were dissolved in 12 mL cold water and each of these solutions were divided into 12 screw cap test tubes each containing 1 mL. These test tubes were kept on ice until ready for use. For each protein, 0.25 mL of concentrated ammonium hydroxide (15 N) was added to each of five of these tubes and 0.25 mL of NaOH (0.5 N) was added to each of five further test tubes. The so prepared samples were incubated at 80° C. for times of 0.5, 3, 10 and 120 minutes. Thereafter the mixture was frozen and lyophilized to dryness. After the sample preparation the samples were analyzed by electrophoresis on sodium dodecylsulfate-polyacrylamide gels.

The result of the electrophoresis runs was that cross linking of the protein occured in both groups of samples. It was found, however, that the rate of cross linking is much slower with ammonium hydroxide than with sodium hydroxide despite the fact that ammonium hydroxide was present in a 30 fold excess to that of the sodium hydroxide. Furthermore, the amount of cross linking with concentrated ammonium hydroxide was much less than that utilizing diluted sodium hydroxide. This is a further reason why presently ammonium hydroxide is the preferred base for the extraction of NARP.

Reasonable variations and modifications which will become apparent to those skilled in the art can be made in this invention without departing from the spirit and scope thereof.

I claim:

1. A process for producing nucleic acid reduced protein (NARP) from a single cell protein (SCP) mixture comprising (a) subjecting an SCP mixture containing single cells with high nucleic acid content and a liquid to a nucleic acid removal step wherein said SCP mixture is heated with a mineral acid at temperatures between about 50° C. and about 100° C. so at least a significant portion of the nucleic acid in the single cells is transferred to said liquid while the single cells remain essentially intact thus producing a mixture of cells with reduced mucleic acid content and a nucleic acid containing fluid, (b) separating said cells with reduced nucleic acid content from said nucleic acid containing fluid, (c) extracting the cells with reduced nucleic acid content with base at a pH of about 10.6 or more to obtain a NARP mixture of a liquid and a solid phase, (d) separating the liquid phase being essentially free of insoluble cellular material and the solid phase being essentially free of the liquid, (e) recovering said liquid phase as a NARP solution and the first product of the process, and (f) recovering the solid phase as a NARP cell product and the second product of the process.

2. A process in accordance with claim 1 wherein said SCP mixture is contacted with $H_2SO_4$.

3. A process in accordance with claim 1 wherein said SCP mixture is contacted with $H_3PO_4$ and said first separation step (b) is carried out only after prior neutralization of said nucleic acid containing fluid.

4. A process in accordance with claim 1 wherein prior to said first separation step (b) said mixture containing nucleic acids is neutralized to a pH of about 5 and 10 and only thereafter said cells with reduced nucleic acid content are separated from said nucleic acid containing fluid.

5. A process in accordance with claim 1 wherein said SCP mixture is obtained by subjecting a mixture of a microorganism and a growth medium to fermentation conditions in a fermentation zone and said SCP mixture is at least a portion of the effluent from said fermentation zone.

6. A process in accordance with claim 5 wherein said microorganism used is a yeast.

7. A process in accordance with claim 5 wherein at least a portion of said nucleic acid containing fluid is introduced into said fermentation zone.

8. A process in accordance with claim 7 wherein said step (a) is carried out by subjecting said single cell protein mixture to a treatment with an acid and heat and wherein said acid is neutralized with an oxide, hydroxide, carbonate or bicarbonate of a metal or equivalent of metal present in said growth medium as minerals or trace minerals.

9. A process in accordance with claim 8 wherein said acid is a mineral acid, the anion of said acid being the same as the anion of said minerals or trace minerals.

10. A process in accordance with claim 8 wherein said neutralization is carried out prior to said first separation step (b).

11. A process in accordance with claim 1 wherein said extraction is carried out with a 0.5 N to 15 N base.

12. A process in accordance with claim 11 wherein said extraction is carried out with $NH_4OH$.

13. A process for the production of cells of reduced nucleic acid content comprising (a) subjecting a microorganism and a minerals containing growth medium for said microorganism together to fermentation conditions in a fermentation zone, (b) withdrawing an effluent containing said microorganism and growth medium from said fermentation zone and introducing said effluent into an acidifying zone wherein said effluent is contacted with a mineral acid under suitable conditions to remove at least a portion of the nucleic acids contained in the cells of said microorganism into the surrounding fluid, (c) withdrawing from said acidifying zone an acidified mixture of a nucleic acid containing liquid phase and a solid cell phase, the cells of said solid cells phase having a reduced nucleic acid content but an essentially unchanged protein content as compared to the cells in the liquid phase.

(d) separating in a separation zone the liquid phase and the solid cell phase into a cell rich phase and a liquid phase essentially free of microbial cells, (e) withdrawing said liquid phase from said separation zone, (f) neutralizing said liquid phase prior to the introduction thereof into the fermentation zone with an oxide, hydroxide, carbonate, or bicarbonate of one or more metals or equivalents of metals, the mineral acid and the metals being selected so that the mineral acid anion and the metal together will form one or more of the minerals already present or desired in said growth medium, (g) introducing at least a portion of the neutralized nucleic acid containing liquid phase into said fermentation zone, (h) subjecting the solid cell phase cells with reduced nucleic acid content to an extraction with a base at a pH of about 10.6 or higher to obtain a liquid and solid phase, (i) separating said liquid and solid phase into a liquid phase containing the extracting protein and a proteinaceous solid phase, (j) drying said liquid phase containing the extracted protein and said proteinaceous solid phase individually so as to obtain NARP products use.

14. A process in accordance with claim 13 wherein said mineral acid is selected from the group consisting of sulfuric acid, hydrochloric acid, phosphoric acid and said neutralization step is carried out with a base selected from the group consisting from the hydroxides or carbonates of sodium, potassium, calcium, magnesium and ammonium and mixtures thereof.

15. A process in accordance with claim 13 wherein the base in extraction step (h) is ammonium hydroxide.

16. A process in accordance with claim 15 wherein, the ammonia values are removed during product drying steps (j) are recycled back to the fermenter.

* * * * *